(12) United States Patent
Ferrari et al.

(10) Patent No.: US 10,844,047 B2
(45) Date of Patent: Nov. 24, 2020

(54) PROCESS FOR THE PREPARATION OF BAZEDOXIFENE

(71) Applicant: ERREGIERRE S.p.A., San Paolo d'Argon (IT)

(72) Inventors: Massimo Ferrari, Cenate Sotto (IT); Daniele De Zani, Roncello (IT); Stefano Vezzosi, Verolanuova (IT); Paolo Belotti, S. Paolo d'Argon (IT)

(73) Assignee: ERREGIERRE S.p.A., San Paolo d'Argon (IT)

( * ) Notice: Subject to any disclaimer, the term of this patent is extended or adjusted under 35 U.S.C. 154(b) by 0 days.

(21) Appl. No.: 16/445,474

(22) Filed: Jun. 19, 2019

(65) Prior Publication Data

US 2019/0389842 A1 Dec. 26, 2019

(30) Foreign Application Priority Data

Jun. 21, 2018 (IT) .................. 102018000006562

(51) Int. Cl.
| | |
|---|---|
| *C07D 209/10* | (2006.01) |
| *C07D 265/28* | (2006.01) |
| *C07D 403/10* | (2006.01) |
| *C07D 403/12* | (2006.01) |

(52) U.S. Cl.
CPC ......... *C07D 403/12* (2013.01); *C07D 209/10* (2013.01)

(58) Field of Classification Search
CPC .. C07D 209/10; C07D 265/28; C07D 403/10; C07D 403/12
See application file for complete search history.

(56) References Cited

U.S. PATENT DOCUMENTS 6,380,166 B1 4/2002 Miller et al.

FOREIGN PATENT DOCUMENTS

| CN | 104098499 B | 5/2016 |
|---|---|---|
| GB | 933507 A | 8/1963 |
| WO | 2008098527 A1 | 8/2008 |

OTHER PUBLICATIONS

Chiti W et al., "Su alcuni derivati del p-ossipropiofenone ad attivita' anestetica locale", Il Farmaco Ed. Scientifica, No. 12, Dec. 1, 1960, pp. 773-787.
Search Report of IT201800006562 dated Feb. 21, 2019.
Takashi T., "Propiophenone", Nippon Yakurigaku Zasshi, vol. 58, Jan. 1, 1962, pp. 67-77.

*Primary Examiner* — Brenda L Coleman
(74) *Attorney, Agent, or Firm* — Silvia Salvadori, P.C.; Silvia Salvadori

(57) ABSTRACT

The invention relates to a process for preparation of the compound 3-methyl-5-benzyloxy-2-(4-benzyloxyphenyl)-1H-indole 5, an intermediate for the synthesis of bazedoxifene and bazedoxifene acetate.

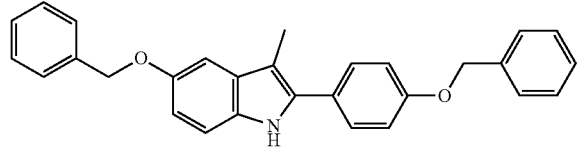

6 Claims, No Drawings

PROCESS FOR THE PREPARATION OF BAZEDOXIFENE

This Non-Provisional application claims priority to and the benefit of Italian Application No. 102018000006562 filed on 21 Jun. 2018, the content of which is incorporated herein by reference in its entirety.

FIELD OF INVENTION

The present invention relates to a process for preparation of the compound 3-methyl-5-benzyloxy-2-(4-benzyloxyphenyl)-1H-indole 5, an intermediate for the synthesis of bazedoxifene and the analogues thereof.

BACKGROUND TO THE INVENTION

Bazedoxifene acetate (1-[4-(2-azepan-1-yl-ethoxy)benzyl]-2-(4-hydroxyphenyl)-3-methyl-5-hydroxyindole acetate) of formula 1 is a selective oestrogen receptor modulator (SERM), registered in Europe for the treatment of post-menopausal osteoporosis in women at increased risk of fractures.

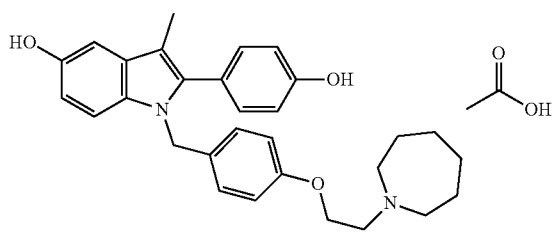

1

The compound acts as receptor agonist and/or antagonist, depending on the type of cell and tissue. Its effects are oestrogen-like in the bone (reduction of biochemical markers of bone turnover and resorption) and liver (reduction of LDL cholesterol and lipoproteins), and anti-oestrogenic in the endometrium and breast. Studies are currently being conducted on its potential use in the treatment of breast and pancreatic cancer.

The preparation of bazedoxifene and the salts thereof is described in numerous patent documents, such as U.S. Pat. Nos. 5,998,402, 6,479,535, 6,005,102, EP 0802183 B 1, EP 1025077 B, WO 2011022596 A2 and WO2008/098527 A1, and in the publication *Journal of Medicinal Chemistry*, Vol 44, 1564-1567, 2001.

The key intermediate for the majority of the syntheses described is the compound 3-methyl-5-benzyloxy-2-(4-benzyloxyphenyl)-1H-indole 5, obtained by the synthesis method reported in Scheme 1, wherein the key step is the Bischler-Möhlau reaction between 1-(4-benzyloxyphenyl)-2-(4-benzyloxyphenylamino)propan-1-one of formula 4 and 4-benzyloxyaniline hydrochloride of formula 2. The compound of formula 4, in turn, is obtained from 4-benzyloxyaniline hydrochloride 2 and 4-benzyloxyphenyl-2-bromopropan-1-one of formula 3.

Scheme 1

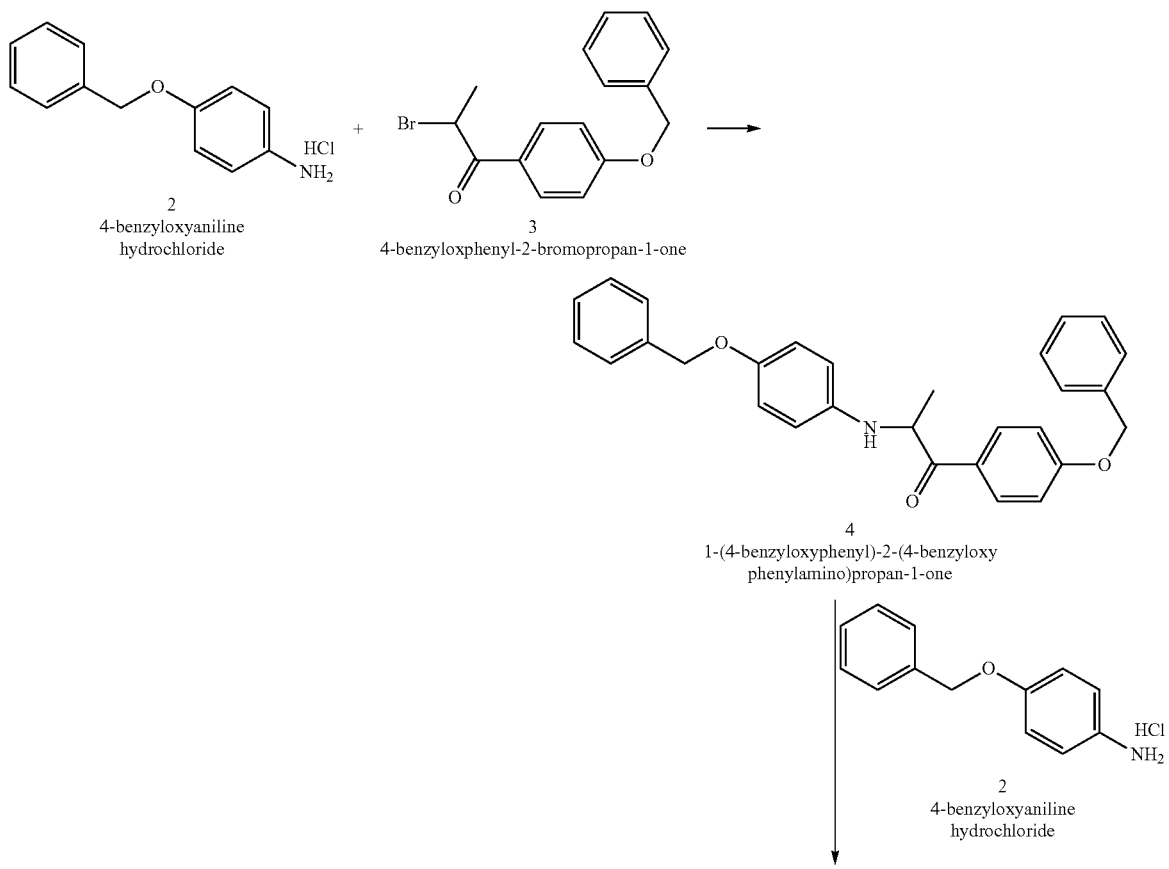

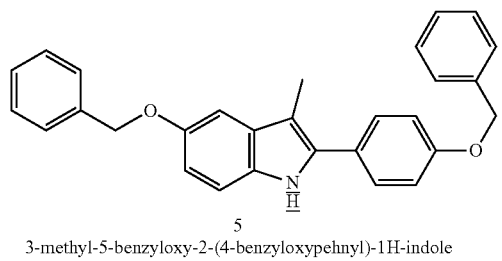

5
3-methyl-5-benzyloxy-2-(4-benzyloxypehnyl)-1H-indole

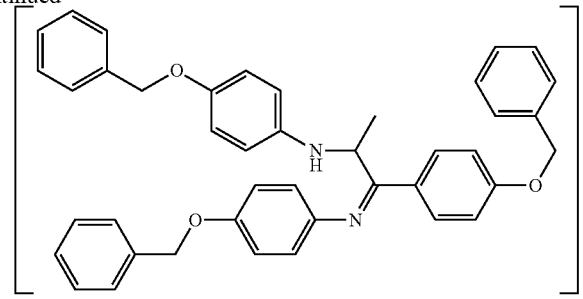

WO2008/098527 A1 describes a method for the preparation of the compound of formula 5 by reacting the bromine derivative of formula 3 and the aniline of formula 2, wherein the intermediate 1-(4-benzyloxyphenyl)-2-(4-benzyloxyphenylamino)propan-1-one of formula 4 is isolated and then subjected to the Bischler-Möhlau reaction with the compound of formula 2.

Intermediate 5 is then converted to bazedoxifene acetate by the synthesis method reported in Scheme 2, which involves alkylation of 5 with 1-[2-[4-(chloromethyl)phenoxy]ethyl]azepane of formula 6 to give intermediate 7. Catalytic hydrogenation of 7 provides bazedoxifene 8, which is finally salified with acetic acid to give 1.

Scheme 2

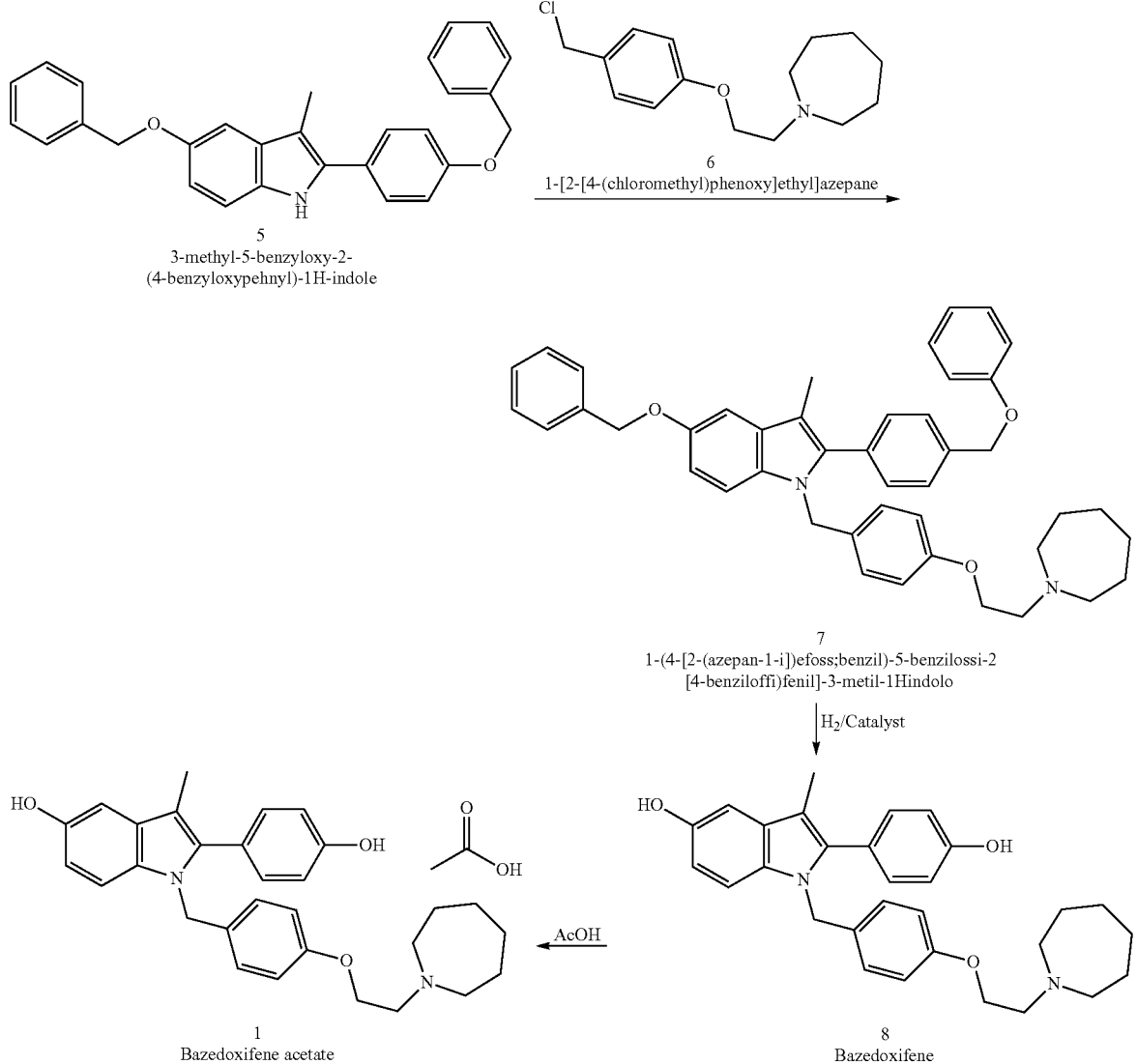

The Bischler-Möhlau reaction is a general procedure used to prepare 2-aryl-indoles from an α-bromine-alkyl-arylketone such α-bromoacetophenone or α-bromopropiophenone, and an excess (at least two molar equivalents per bromoketone equivalent) of an aniline (Bischler, A.; Brion, H. *Ber. Dtsch. Chem. Ges.* 1892, 25, 2860-2879; Bischler, A.; Fireman, P. *Ber. Dtsch. Chem. Ges.* 1893, 26, 1336-1349).

The method originally developed requires fairly drastic reaction conditions, and variations thereon involving milder conditions, such as the use of lithium bromide as catalyst or irradiation with microwaves, have therefore been developed. Variations on the synthesis are also known which allow the preparation of indoles not substituted in the 2 and 3 positions by acetal cyclisation (Pchalek, K. et al., *Tetrahedron* 2005, 61, 77-82; Sridharan, V. et al., *Synlett* 2006, 91-95; Nordlander, J. E. et al., *J. Org. Chem.* 1981, 46, 778-782; Sundberg, R. J. et al., *J. Org. Chem.* 1984, 49, 249-254).

In addition to α-aniline ketones, such as the non-isolated intermediate 4 described in Scheme 1, or isolated in WO2008/098527, which are the classic intermediates for the synthesis of 2-aryl-indoles using the Bischler-Möhlau reaction, the only intermediates, whether isolated and not, described in the literature for this reaction to date are α-ammonium ketones or α-pyridinium ketones. The general structures of the intermediates known to date for the Bischler-Möhlau synthesis are reported in Scheme 3.

Scheme 3

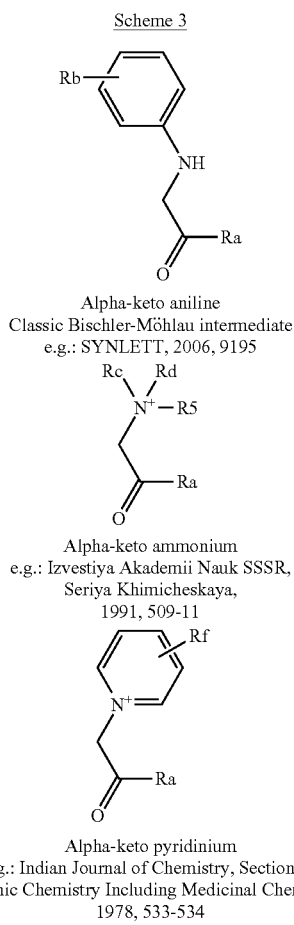

Alpha-keto aniline
Classic Bischler-Möhlau intermediate
e.g.: SYNLETT, 2006, 9195

Alpha-keto ammonium
e.g.: Izvestiya Akademii Nauk SSSR,
Seriya Khimicheskaya,
1991, 509-11

Alpha-keto pyridinium
e.g.: Indian Journal of Chemistry, Section B:
Organic Chemistry Including Medicinal Chemistry,
1978, 533-534

Ra: alkyl or aryl
Rb: H or generic substituents
Rc, Rd, Re: various alkyls, for example Rc = Rd = Re = Methyl
Rf: H or alkyl The use of aryl-alkylketone intermediates substituted in the alpha position with primary or secondary aliphatic/cycloaliphatic amines, such as α-monoalkylamino or α-bisalkylamino acetophenones or propiophenones, or with heterocycloalkyl amines, to obtain generic indoles, in particular the compound of formula 5, via the Bischler-Möhlau reaction, is not known.

DESCRIPTION OF THE INVENTION

It has now been discovered that compounds of formula (I)

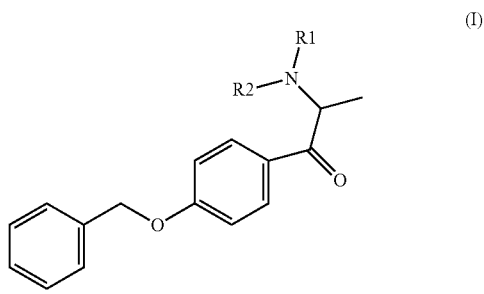

(I)

wherein $R_1$ and $R_2$ are, independently of one another, selected from the group containing hydrogen, $C_1$-$C_4$ alkyl and $C_3$-$C_7$ cycloalkyl, on the proviso that $R_1$ and $R_2$ are not both hydrogen; or $R_1$ and $R_2$, taken together with the nitrogen atom to which they are bonded, form a heterocycloalkyl ring selected from the group containing pyrrolidine, piperidine and morpholine;

are intermediates useful for the preparation of the compound 3-methyl-5-benzyloxy-2-(4-benzyloxyphenyl)-1H-indole 5, an intermediate for the synthesis of bazedoxifene 8 and bazedoxifene acetate 1.

DETAILED DESCRIPTION OF THE INVENTION

The invention relates to a process for the synthesis of bazedoxifene 8 or bazedoxifene acetate 1, comprising the following steps:

a) Bischler-Möhlau reaction between a compound of formula (I)

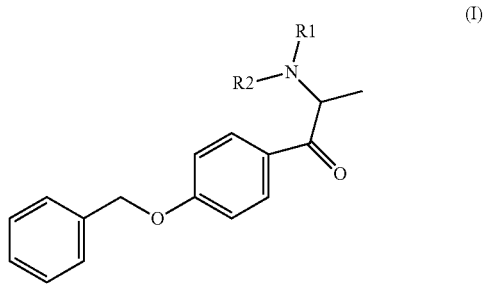

(I)

wherein $R_1$ and $R_2$, independently of one another, are selected from the group containing hydrogen, $C_1$-$C_4$ alkyl and $C_3$-$C_7$ cycloalkyl, on the proviso that $R_1$ and $R_2$ are not both hydrogen; or $R_1$ and $R_2$, taken together with the nitrogen atom to which they are bonded, form a heterocycloalkyl ring selected from the group containing pyrrolidine, piperidine and morpholine;

and a compound of formula (II)

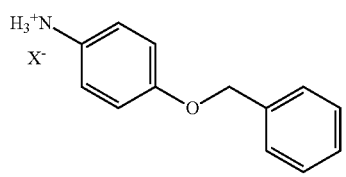

wherein X⁻ represents the anion of an organic or inorganic acid;
to give the compound 3-methyl-5-benzyloxy-2-(4-benzyloxyphenyl)-1H-indole of formula 5

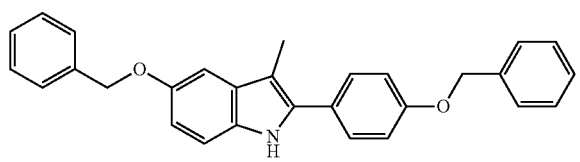

b) conversion of 5 to bazedoxifene 8 or bazedoxifene acetate 1 by known methods.

In one embodiment of the invention, $R_1$ and $R_2$, taken together with the nitrogen atom to which they are bonded, form a heterocycloalkyl ring as defined above.

In a preferred embodiment of the invention, $R_1$ and $R_2$, taken together with the nitrogen atom to which they are bonded, form a morpholine ring.

The process for preparation of the compounds of formula (I) is summarised in Scheme 4 below, wherein 4-benzyloxyphenylpropiophenone 9 is reacted with a brominating agent to give 4-benzyloxyphenyl-2-bromopropan-2-one of formula 3. Bromoketone 3 is then reacted with a primary or secondary amine of formula (IV) wherein $R_1$ and $R_2$ are defined as for the compounds of formula (I), to give a compound of formula (I). Compound (I) can optionally be isolated, or can be reacted in situ with a compound of formula (II) under the classic conditions of the Bischler-Möhlau reaction to give the compound of formula 5.

Scheme 4

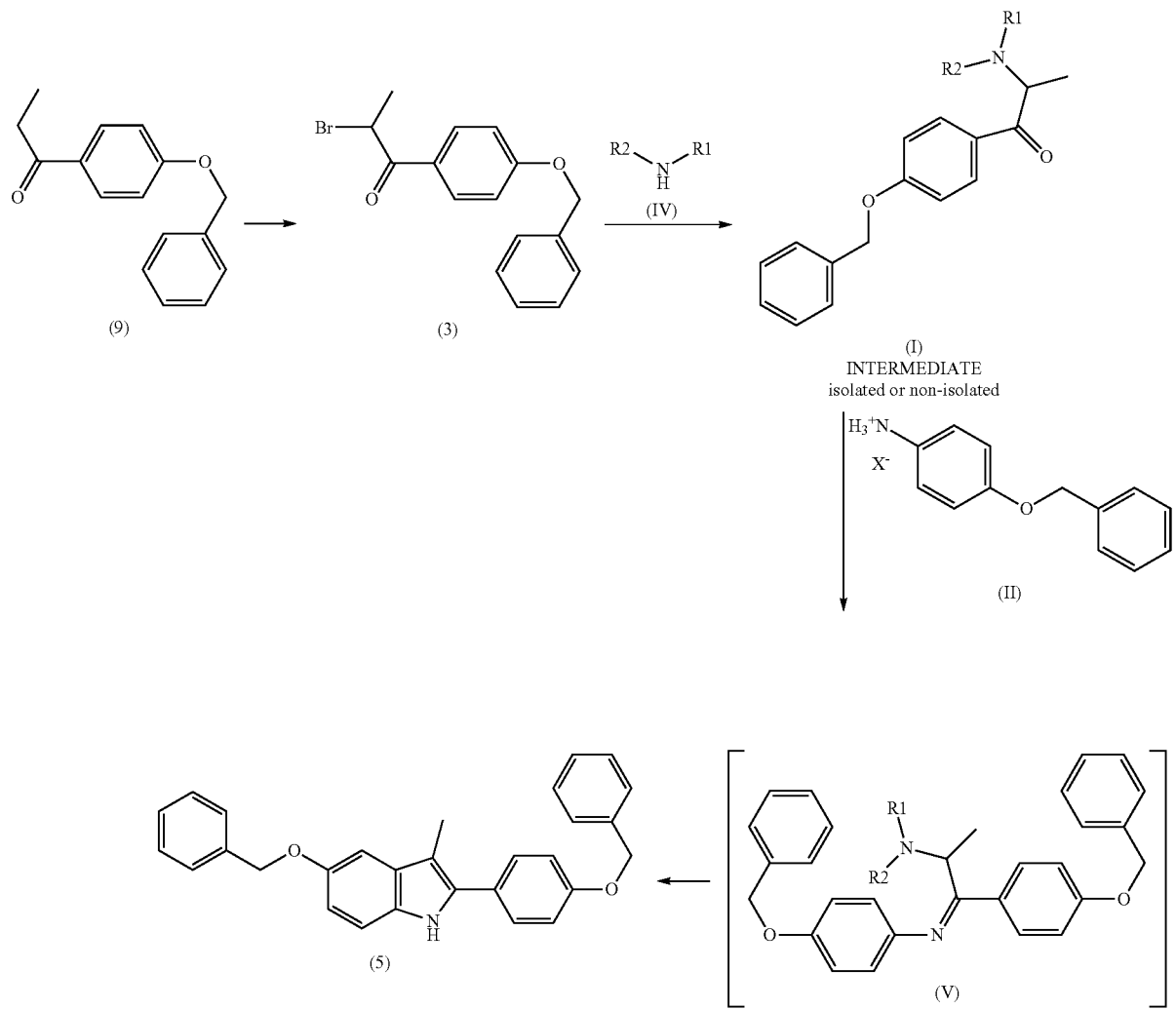

4-benzyloxypropiophenone 9 can be converted to 4-benzyloxyphenyl-2-bromopropan-1-one 3 by conventional methods for bromination of a methylene group adjacent to a carbonyl group, for example with bromine in the presence of a Lewis acid such as aluminium trichloride, in a solvent selected from toluene, methanol or mixtures thereof. The reaction of bromoketone 3 with an amine (IV) is generally conducted with at least two molar equivalents of (IV) per molar equivalent of 3, in the absence of solvent or in a solvent selected from toluene, chlorobenzene, ethyl acetate, N,N-dimethylformamide and N,N-dimethylacetamide, preferably toluene. The reaction is preferably conducted in the absence of solvent.

The Bischler-Möhlau reaction between a compound of formula (I) and a compound of formula (II) can be conducted in the solvents typically used for said reaction, such as N,N-dimethylformamide (DMF), N,N-dimethylacetamide (DMA), toluene and chlorobenzene, operating at the reflux temperature of said solvents. The inventors of the present application have found that using chlorobenzene instead of DMF, the solvent normally used for this step, prevents the formation of the N-formyl derivative of aniline (II), which is caused by the breakdown of DMF at the high temperatures essential for cyclisation. Said N-formyl derivative represents an additional impurity to be eliminated from the end product, and above all, removes aniline (II) from the reaction. The use of chlorobenzene is particularly preferred.

In the process according to the invention, 1.1 molar equivalents of aniline derivative (II) compared with the compound of formula (I) are typically used for the preparation of the compound of formula 5, as opposed to the 2.2 equivalents required when the classic method starting with an α-bromo-alkyl-arylketone is used.

Moreover, the compounds of formula (I) which are to undergo Bischler-Möhlau cyclisation are obtained from aliphatic, cycloaliphatic or heterocycloalkyl amines, which are cheaper than the aniline derivatives typically used for the preparation of α-aniline ketone intermediates.

The yield and purity of the compound of formula 5 are greater than those obtained by the classic method if the intermediates of formula (I) are isolated before undergoing cyclisation.

The yield and purity of the compound of formula 5 are comparable with those of the classic method if intermediates (I) are not isolated, but in any event the process according to the invention is economically advantageous in view of the factors reported above.

1-(4-benzyloxyphenyl)propan-1-one 9 can be prepared by reacting 1-(4-hydroxyphenyl)propan-1-one of formula 10

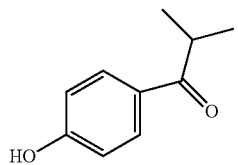

with benzyl chloride.

The reaction is typically conducted under the classic conditions of alkylation of phenol groups, operating in an organic solvent such as toluene, chlorobenzene or DMF, or under phase-transfer conditions in a mixture of water and a solvent immiscible with water such as toluene or chlorobenzene in the presence of a tetraalkylammonium halide, with or without the presence of methyl cellosolve. The reaction is conducted in the presence of an organic or inorganic base such as an alkali or alkaline-earth metal hydroxide, or a carbonate, an alkoxide or an alkali metal hydride. Step a) is preferably conducted in a mixture of water and toluene using sodium hydroxide as base, in the presence of tetrabutylammonium bromide.

In one embodiment of the invention, the compound of formula (I) is selected from:
1-(4-benzyloxyphenyl)-2-(piperidin-1-yl)propan-1-one;
1-(4-benzyloxyphenyl)-2-(pyrrolidine-1-yl)propan-1-one;
1-(4-benzyloxyphenyl)-2-morpholin-4-yl-propan-1-one;
1-(4-benzyloxyphenyl)-2-diethylaminopropan-1-one;
1-(4-benzyloxyphenyl)-2-cyclohexylaminopropan-1-one.

In one embodiment of the invention, the compound of formula (I) is 1-(4-benzyloxyphenyl)-2-(morpholin-4-yl)propan-1-one.

3-methyl-5-benzyloxy-2-(4-benzyloxyphenyl)-1H-indole 5 can be converted to bazedoxifene 8 or bazedoxifene acetate 1 by any of the processes described for the preparation of bazedoxifene 8 or bazedoxifene acetate 1, for example by the method described in Scheme 2 above, comprising the following steps:

N-alkylation of 3-methyl-5-benzyloxy-2-(4-benzyloxyphenyl)-1H-indole 5 with 1-[2-[4-(chloromethyl)phenoxy]ethyl]azepane 6 to give the compound 1-{4-[2-(azepan-1-yl)ethoxy]benzyl}-5-(benzyloxy)-2-[4-(benzyloxy)phenyl]-3-methyl-1H-indole 7;

removal of the benzyloxy groups from compound 7 to give bazedoxifene 8, and optional conversion thereof to its acetate salt 1.

In one embodiment, in the process according to the invention for preparation of bazedoxifene or bazedoxifene acetate, the compound 3-methyl-5-benzyloxy-2-(4-benzyloxyphenyl)-1H-indole 5 is obtained from a compound selected from:
1-(4-benzyloxyphenyl)-2-(piperidin-1-yl)propan-1-one;
1-(4-benzyloxyphenyl)-2-(pyrrolidine-1-yl)propan-1-one;
1-(4-benzyloxyphenyl)-2-morpholin-4-yl-propan-1-one;
1-(4-benzyloxyphenyl)-2-diethylaminopropan-1-one;
1-(4-benzyloxyphenyl)-2-cyclohexylaminopropan-1-one.

In the process according to the invention for preparation of bazedoxifene or bazedoxifene acetate, the compound 3-methyl-5-benzyloxy-2-(4-benzyloxyphenyl)-1H-indole 5 is preferably obtained from 1-(4-benzyloxyphenyl)-2-(morpholin-4-yl)propan-1-one.

As detailed in the Comparative Example reported in the present application, the process according to the invention for preparation of intermediate 5 presents numerous advantages over the process described in WO2008/098527, performing far better than the latter in terms of the purity of the isolated compound 5, as well as being simpler to conduct on an industrial scale.

In particular, by following the method described in WO2008/098527, an intermediate 5 is obtained with much lower HPLC purity (total impurities 3.35%) than that of the intermediate obtained by the process according to the invention (total impurities 0.24-0.29%). It should be noted that the main impurity present in intermediate 5 obtained according to WO2008/098527 is 4-benzyloxyaniline, which is a potentially genotoxic impurity. Its content amounts to 1.97%, which is much higher than the content found in intermediate 5 obtained by the process according to the invention (0.01%).

Moreover, the process of WO2008/098527 involves two filtrations in the N-(4-benzyloxyphenyl)-α-amino-4-benzyloxypropiophenone 4 preparation step, and the subsequent Bischler-Möhlau reaction is conducted in isopropanol at 110-115° C., or under pressure (3-4 bars), whereas the method according to the present invention only involves one isolation of the compounds of formula (I), and the Bischler-Möhlau reaction is conducted at atmospheric pressure, and therefore under safer conditions.

Finally, the intermediates of formula (I) of the process according to the invention are obtained by using aliphatic, cycloaliphatic or heterocycloalkyl amines, which are liquids, whereas intermediate 4 of WO2008/098527 is a solid. In the case of preparation of the intermediates of formula (I) according to the invention, in particular intermediate (I) wherein $NR_1R_2$ represents a morpholine ring (compound 11), the excess amine (morpholine) is therefore easily eliminated. Conversely, the 4-benzyloxyaniline used to prepare intermediate 4 of WO2008/098527 is a solid difficult to eliminate, and despite three isolations, the method of WO2008/098527 leads to an indole 5 that contains nearly 2% thereof, as against the 0.01% quantified in indole 5 obtained by the process according to the invention. The technical advantage is obvious.

A further subject of the invention is the compound of formula (I) 1-(4-benzyloxyphenyl)-2-morpholin-4-yl-propan-1-one 11.

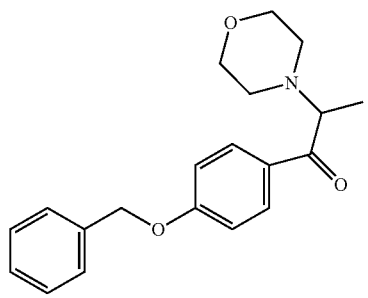

11

The invention will now be illustrated by the following examples.

Example 1—Preparation of 1-(4-benzyloxyphenyl)-2-morpholin-4-yl-propan-1-one 11

Step I: Preparation of 4-benzyloxypropiophenone

Distilled water (15 Kg), sodium hydrate (4.50 Kg; 0.1125 moles), toluene (57.0 Kg), 4-hydroxypropiophenone (15.0 Kg; 0.10 moles) and tetrabutylammonium bromide (0.75 Kg) are loaded into a reactor. The mass is reflux heated (about 90° C.), and benzyl chloride (14.25 Kg; 0.1125 moles) is then added. The mass is maintained at reflux until complete conversion, and the aqueous phase is then separated and eliminated. The resulting toluene solution is cooled to 15-25° C. and sent to the next step without further processing.

Step II: Preparation of 4-benzyloxy-α-bromopropiophenone

The whole of the toluene solution of 4-benzyloxy-propiophenone obtained in Step I from 15.0 Kg of 4-hydroxypropiophenone, methanol (24.0 Kg) and aluminium chloride are loaded into a reactor in catalytic amounts. The mass is heated to 40-45° C. and, while maintaining said temperature, bromine (17.25 Kg; 0.108 moles) is poured in. After pouring, the mass is maintained at 40-45° C. until complete conversion, and distilled water is then added.

The lower aqueous phase is separated and eliminated, and the resulting toluene solution is sent to the next step without further processing.

Step III: Preparation of 1-(4-benzyloxyphenyl)-2-morpholin-4-yl-propan-1-one

The whole of the toluene solution of 4-benzyloxy-α-bromopropiophenone obtained in Step II from 15.0 Kg (0.10 moles) of 4-hydroxypropiophenone and morpholine (18.0 Kg; 0.2066 moles) are loaded into a reactor. The mass is reflux heated (about 110° C.) for 2 hours, and distilled water is then added to the mass. The aqueous phase is separated and discarded.

The organic phase is distilled under vacuum until an oily residue is obtained and methanol (90 Kg) is then poured in. The mass is stirred at 55-65° C. until a complete solution is obtained, which is cooled to 10° C. The precipitated mass is centrifuged, washed with methanol and dried. 26.0 Kg of 1-(4-benzyloxyphenyl)-2-morpholin-4-yl-propan-1-one is obtained. Yield: 80.0%, calculated on the Kg of 4-hydroxypropiophenone used in Step I.

HPLC analysis shows a total impurity content of 0.64%.

Example 2

By following the procedure described in example 1 and replacing the morpholine in Step III with an amine selected from piperidine, pyrrolidine, diethylamine and cyclohexylamine, the following products are prepared:
1-(4-benzyloxyphenyl)-2-(piperidin-1-yl)propan-1-one;
1-(4-benzyloxyphenyl)-2-(pyrrolidine-1-yl)propan-1-one;
1-(4-benzyloxyphenyl)-2-diethylaminopropan-1-one;
1-(4-benzyloxyphenyl)-2-cyclohexylaminopropan-1-one.

Example 3—Preparation of 1-(4-benzyloxyphenyl)-2-morpholin-4-yl-propan-1-one 11

The procedure described in example 1 is repeated, isolating 4-benzyloxy-α-bromopropiophenone 3 in Step II and then reacting it with morpholine.

1-(4-benzyloxyphenyl)-2-morpholin-4-yl-propan-1-one 11 is obtained with a yield of 90.2%.

HPLC analysis shows a total impurity content of 0.12%.

Example 4—Preparation of 3-methyl-5-benzyloxy-2-(4-benzyloxyphenyl)-1H-indole 5

The 1-(4-benzyloxyphenyl)-2-morpholin-4-yl-propan-1-one obtained in example 1 (26.0 Kg; 0.08 moles), chlorobenzene (104 Kg) and 4-(benzyloxy)aniline hydrochloride (20.8 Kg; 0.088 moles) are loaded into a reactor. The mass is heated at 125-130° C. for 8 hours. The mass is then cooled to 80-90° C., and distilled water is added to it. The lower organic phase is separated, and the upper aqueous phase is eliminated. The organic phase is distilled to residue, and methanol (104 Kg) is then added. The mass is cooled to 20-25° C. and then centrifuged, washing with methanol. After drying, 28.0 Kg of 3-methyl-5-(benzyloxy)-2-(4-benzyloxyphenyl)-1H-indole is obtained. Yield: 83.5%.

HPLC analysis shows a total impurity content of 0.24%.
The 4-(benzyloxy)aniline content amounts to 0.01%.

Example 5—Preparation of 3-methyl-5-benzyloxy-2-(4-benzyloxyphenyl)-1H-indole 5

The procedure described in example 4 is repeated, using the 1-(4-benzyloxyphenyl)-2-morpholin-4-yl-propan-1-one 11 obtained in example 3 as starting product.

3-methyl-5-benzyloxy-2-(4-benzyloxyphenyl)-1H-indole 5 is obtained with a yield of 83.5% compared with intermediate 11, and a yield of 75% compared with bromine derivative (3).

HPLC analysis shows a total impurity content of 0.29%. The 4-(benzyloxy)aniline content amounts to 0.01%.

Example 6

The procedure described in example 4 is repeated, reacting 4-benzyloxyaniline hydrochloride with the alpha-aminopropiophenones obtained in example 2, to give the compound 3-methyl-5-benzyloxy-2-(4-benzyloxyphenyl)-1H-indole 5.

Example 7—Preparation of bazedoxifene acetate

Step I: Preparation of 1-{4-[2-(azepan-1-yl)ethoxy]benzyl}-5-(benzyloxy)-2-[4-(benzyloxy)phenyl]-3-methyl-1H-indole 60% sodium hydride (6.0 Kg; 0.15 moles) and N,N-dimethylacetamide (10.0 Kg) are loaded into a neutralised reactor. The temperature is adjusted to 0-10° C., and a separately prepared solution of 3-methyl-5-(benzyloxy)-2-(4-benzyloxyphenyl)-1H-indole (25.0 Kg, 0.0596 moles) and N,N-dimethylacetamide (37.5 Kg) is dripped in. A solution prepared separately by dissolving 1-{2-[4-(chloromethyl)phenoxy]ethyl}hexahydro-1H-azepine hydrochloride (20.0 Kg; 0.0657 moles) and N,N-dimethylacetamide is then poured in. After pouring, the mass is maintained at 0-10° C. for 30 min, and toluene (50 Kg) and water are then added. The mass is heated to 70° C., and the lower aqueous phase is then separated and eliminated. Methanol (175 Kg) is added, and the mixture is cooled to 20-25° C. and centrifuged, washing with methanol (50 Kg). After drying, about 32.0 kg of 1-{4-[2-(azepan-1-yl)ethoxy]benzyl}-5-(benzyloxy)-2-[4-(benzyloxy)phenyl]-3-methyl-1H-indole is obtained. Yield: 82.6%.

Step II: Preparation of bazedoxifene acetate

1-{4-[2-(azepan-1-yl)ethoxy]benzyl}-5-(benzyloxy)-2-[4-(benzyloxy)phenyl]-3-methyl-1H-indole (28.0 Kg; 0.043 moles), tetrahydrofuran (140 Kg) and 5% Pd/c (2.80 Kg) are loaded into a reactor. The mixture is hydrogenated at 60° C. and at a hydrogen pressure of 4 atm for 8 hours, and the catalyst is then filtered. The filtered solution is distilled under vacuum, and the resulting oily residue is taken up with distilled water (22.4 Kg), ethyl acetate (67.2 Kg) and 80% acetic acid (3.64 Kg; 0.0485 moles). The mixture is cooled to 20-30° C. to obtain good precipitation, then heated to 0-5° C. and centrifuged, washing with distilled water (22.4 Kg) and ethyl acetate (22.4 Kg). About 20.6 kg of bazedoxifene acetate is obtained. Yield: 90.3%.

Comparative Example 1—Preparation of N-(4-benzyloxyphenyl)-α-amino-4-benzyloxypropiophenone 4

N-(4-benzyloxyphenyl)-α-amino-4-benzyloxypropiophenone 4 is prepared as described in example 2 on page 7 of WO2008/098527, namely the example that reports the highest yield for said product.

In two preparations (Comparative Example 1A and Comparative Example 1B), after a 5 h reaction and isolation by two filtrations, product 4 is obtained with yields of 89.8 and 92% respectively, and a total impurity content of 0.23 and 0.26% respectively.

Comparative Example 2—Preparation of 3-methyl-5-benzyloxy-2-(4-benzyloxyphenyl)-1H-indole 5

Product 4 obtained in Comparative Example 1 is converted to the compound of formula 5 as described in example 2 on page 9 of WO2008/098527, namely the example that reports the highest yield for said product. The reaction is conducted in isopropanol at 110-115° C., under pressure (3-4 bars).

After the 5 h reaction time indicated in WO2008/098527 for the reaction of 4 (obtained from Comparative Example 1A) with 4-benzyloxyaniline hydrochloride, the reaction is incomplete, and product 5 is isolated with a low yield, amounting to 62.4% compared with 4 and 56% compared with bromine derivative 3, and with very low HPLC purity (the sum of all the impurities is 27.3%) (Comparative Example 2A).

By increasing the reaction time until complete conversion is obtained (well over 15 hours), compound 5 is obtained with comparable yields (86.1% compared with 4 [obtained in Comparative Example 1B] and 79.2% compared with bromine derivative 3) to those obtained by the process according to the invention, but with a much lower HPLC purity (the sum of all the impurities is 3.35%, with a 1.97% 4-benzyloxyaniline content) (Comparative Example 2B).

Table 1 compares the yields and purities of intermediate 1-(4-benzyloxyphenyl)-2-morpholin-4-yl-propan-1-one 11 according to the invention (Examples 1 and 3) and intermediate N-(4-benzyloxyphenyl)-α-amino-4-benzyloxypropiophenone 4 of WO2008/098527 (Comparative Example 1).

Table 2 compares the yields and purities of the product 3-methyl-5-benzyloxy-2-(4-benzyloxyphenyl)-1H-indole 5 obtained by the process according to the invention (Examples 4 and 5) or by the process described in WO2008/098527 (Comparative Example 2).

TABLE 1

| | | Starting product | | t | HPLC | Filtrations | % yield | |
|---|---|---|---|---|---|---|---|---|
| Type/Test | Method | 3 | Amine | hours | Total impurities % | no. | Declared | Experimental |
| Example 1 | Invention | not isolated | morpholine | 2 | 0.64 | 1 | 80 | 79.7 |
| Example 3 | Invention* | *isolated | morpholine | 2 | 0.12 | 1 | 80 | 90.2 |
| Comparative Example 1A | WO2008/098527 | isolated | aniline 2 | 5 | 0.23 | 2 | 85 | 89.8 |
| Comparative Example 1B | WO2008/098527 | isolated | aniline 2 | 5 | 0.26 | 2 | 85 | 92 |

*isolating intermediate 3 to have the same conditions as WO2008/098527

TABLE 2

| Example | Method | Starting product | t hours | P Bars | 11 or 4 unreacted | HPLC Aniline 2% | HPLC Total impurities % | Declared yield % from 11 or 4 | Declared yield % from 3 | Experimental yield % from 11 or 4 | Experimental yield % from 3 |
|---|---|---|---|---|---|---|---|---|---|---|---|
| Example 4 | Invention | 11 Obtained in Example 1 | 2 | atm | <2% | 0.1 | 0.24 | 83.5 | / | 85 | / |
| Example 5 | Invention* | 11 Obtained in Example 3 | 2 | atm | <2% | 0.1 | 0.29 | 83.5 | 66.8 | 83.5 | 75 |
| Comparative Example 2A | WO2008/098527 | 4 Obtained in Comparative Example 1A | 5 | 3-4 | >10% | 0.86 | 27.34 | 82 | 69.7 | 62.4 | 56.0 |
| Comparative Example 2B | WO2008/098527** | 4 obtained in Comparative Example 1B | 5 | 3-4 | <2% | 1.97 | 3.35 | 82 | 69.7 | 86.1 | 79.2 |

*isolating intermediate 3 to have the same conditions as WO2008/098527
**increasing the reaction time to have complete conversion (intermediate 4 < 2%)

The invention claimed is:

1. Process for the synthesis of bazedoxifene or bazedoxifene acetate, comprising the following steps:

a) providing a Bischler-Möhlau reaction between a compound of formula (I)

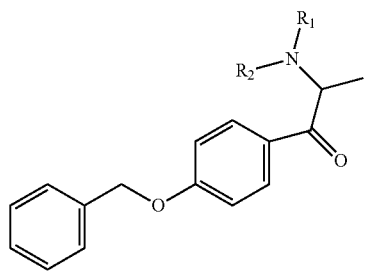

(I)

wherein $R_1$ and $R_2$, independently of one another, are selected from the group containing hydrogen, $C_1$-$C_4$ alkyl and $C_3$-$C_7$ cycloalkyl, on the proviso that $R_1$ and $R_2$ are not both hydrogen; or $R_1$ and $R_2$, taken together with the nitrogen atom to which they are bonded, form a heterocycloalkyl ring selected from the group containing pyrrolidine, piperidine and morpholine;

and a compound of formula (II)

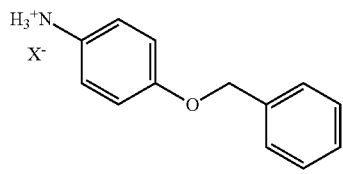

(II)

wherein $X^-$ represents the anion of an organic or inorganic acid;

to give compound 3-methyl-5-benzyloxy-2-(4-benzyloxyphenyl)-1H-indole of formula 5

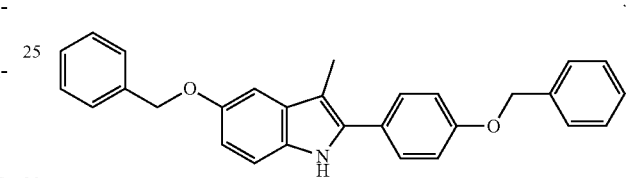

5 b) converting said compound of formula 5 to bazedoxifene or bazedoxifene acetate by a process comprising:
N-alkylation of 3-methyl-5-benzyloxy-2-(4-benzyloxyphenyl)-1H-indole 5 with 1-[2 [4-(chloromethyl)phenoxy]ethyl]azepane to give the compound 1-{4-[2-(azepan-1-yl)ethoxy]benzyl}-5-(benzyloxy)-2-[4-(benzyloxy)phenyl]-3-methyl-1H-indole (compound 7);
removal of the benzyloxy groups from compound 7 to give bazedoxifene, and optional conversion thereof to its acetate salt.

2. Process as claimed in claim 1 wherein $R_1$ and $R_2$, taken together with the nitrogen atom to which they are bonded, form a heterocycloalkyl ring selected from the group containing pyrrolidine, piperidine and morpholine.

3. Process as claimed in claim 2 wherein $R_1$ and $R_2$, taken together with the nitrogen atom to which they are bonded, form a morpholine ring.

4. Process as claimed in claim 1 wherein $X^-$ is a chloride or bromide anion.

5. Process as claimed in claim 4 wherein $X^-$ is the chloride anion.

6. The compound 1-(4-benzyloxyphenyl)-2-morpholin-4-yl-propan-1-one 11

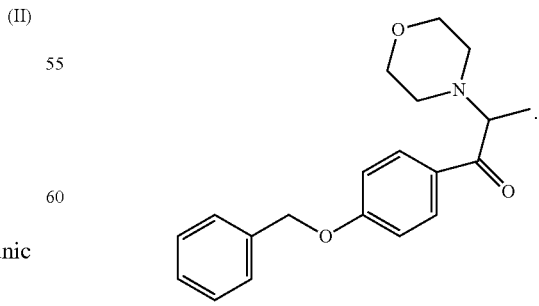

11

* * * * *